United States Patent [19]
Gruber

[11] Patent Number: 6,107,031
[45] Date of Patent: *Aug. 22, 2000

[54] METHOD FOR SCREENING FOR UNKNOWN ORGANISMS

[75] Inventor: Lewis S. Gruber, Chicago, Ill.

[73] Assignee: Hyseq, Inc., Sunnyvale, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/801,174

[22] Filed: Feb. 18, 1997

Related U.S. Application Data

[63] Continuation of application No. 08/332,468, Oct. 31, 1994, abandoned, which is a continuation of application No. 08/097,173, Jul. 23, 1993, abandoned.

[51] Int. Cl.[7] .............................. C12Q 1/68; C07H 21/02; C07H 21/04; C12N 15/00
[52] U.S. Cl. .................................. 435/6; 435/5; 536/23.1; 536/24.3; 935/76; 935/77; 935/78
[58] Field of Search .............................. 435/6, 5; 935/76, 935/77, 78; 536/23.1, 24.3

[56] References Cited

U.S. PATENT DOCUMENTS

| | | |
|---|---|---|
| 4,562,159 | 12/1985 | Shafritz . |
| 4,613,566 | 9/1986 | Potter . |
| 4,677,054 | 6/1987 | White et al. . |
| 4,731,325 | 3/1988 | Palva et al. . |
| 4,766,062 | 8/1988 | Diamond et al. . |
| 4,851,330 | 7/1989 | Kohne ......................................... 435/6 |
| 4,981,783 | 1/1991 | Augenlicht . |
| 5,002,867 | 3/1991 | Macevicz . |
| 5,087,558 | 2/1992 | Webster ...................................... 435/5 |
| 5,202,231 | 4/1993 | Drmanac et al. ............................ 435/6 |
| 5,310,893 | 5/1994 | Erlich et al. . |
| 5,348,855 | 9/1994 | Dattagupta et al. . |
| 5,436,327 | 7/1995 | Southern et al. . |

FOREIGN PATENT DOCUMENTS

| | | |
|---|---|---|
| 0 202 758 A1 | 4/1986 | European Pat. Off. . |
| 0 228 075 A2 | 12/1986 | European Pat. Off. . |
| 0 235 726 A3 | 9/1987 | European Pat. Off. . |
| 0 281 927 A3 | 9/1988 | European Pat. Off. . |
| 0 197 266 B1 | 7/1991 | European Pat. Off. . |
| 0 237 362 B1 | 3/1992 | European Pat. Off. . |
| 0 514 927 | 11/1992 | European Pat. Off. . |
| 497464 A1 | of 1996 | European Pat. Off. . |
| 3506703 C1 | 4/1986 | Germany . |
| WO 86/03782 | 7/1986 | WIPO . |
| 89/109776 | 11/1989 | WIPO . |
| WO 89/10977 | 11/1989 | WIPO . |
| WO 89/11548 | 11/1989 | WIPO . |
| WO 90/04652 | 5/1990 | WIPO . |
| 90/15070 | 12/1990 | WIPO . |
| 92/10588 | 6/1992 | WIPO . |
| 93/04204 | 3/1993 | WIPO . |
| WO 88/03957 | 6/1998 | WIPO .............................. C12Q 1/68 |
| 6425 | 4/1987 | Yugoslavia . |

OTHER PUBLICATIONS

Bainst, W., and Smith, G.C., (1988), "A Novel Method for Nucleic Acid Sequence Determination," Journal of Theoretical Biology, 135: 303–307.

Beltz, G.A., Jacobs, K.A., Eickbush, T.H., Cherbas, P.T., and Kafatos, F.C., (1983), "Isolation of Multigene Families and Determination of Homologies by Filter Hybridization Methods," Methods in Enzymology, 100(19), 266–285.

Conner, B.J., Reyes, A.A., Morin, C., Itakura, K., Teplitz, R.L., and Wallace, R.B., (1983), "Detection of Sickle Cell $\beta^s$–globin Allele by Hybridization with Synthetic Oligonucleotides," Proc. Natl. Acad. Sci. USA, 80, 278–282.

Hobden, A.N., Read, M.J., Dykes, C.W., and Harford S., (1984), "M13 Clones Carrying Point Mutations: Identification by Solution Hybridization," Analytical Biochemistry, 144, 75–78.

Matthews, J.A., Kricka, L.J., (1988), "Analytical Strategies for the Use of DNA Probes," Review Article, Analytical Biochemistry, 169, 1–25.

Meinkoth, J., and Wahl, G., (1984), "Hybridization of Nucleic Acids Immobilized on Solid Supports," Review Article, Analytical Biochemistry, 138, 267–284.

Poustka, A., Phol, T., Barlow, D.P., Zehetner, G., Craig, A., Michiels, F., Ehrich, E., Frischauf, A.M., and Lehrach, H., (1986), "Molecular Approaches to Mammalian Genetics," Cold Spring Harbor Symposia on Quantitative Biology, LI, 131–139.

Syvanen, A.C., (1986), "Nucleic Acid Hybridization: From Research Tool to Routine Diagnostic Method," Review Article, Medical Biology, 64, 313–324.

Drmanac, R., Labat, I., Brukner, I., and Crkvenjakov, R., (1989), "Sequencing a Megabase Plus DNA by Hybridization: Theory of the Method," Genomics, 4, 114–128.

Gusev, V.D., Kulichkov, V.A., and Titkova, T.N., (1980), "Analysis of Genetic Texts. I. 1–Gram Characteristics," Emperical Prediction and Recognition of Patterns, 83, 11–33.

Saiki, R.K., Walsh, P.S., Levenson, C.H., Erlich, H.A., (1989), "Genetic Analysis of Amplified DNA with Immobilized Sequence–Specific Oligonucleotide Probes," Proc. Natl. Acad. Sci. USA, 86, 6230–6234.

Drmanac, R., Labat, I., Strezoska, Z., Paunesku, T., Radosavljevic, D., Drmanac, S., and Crkvenjakov, R., (1990), "Sequencing by Oligonucleotide Hybridization: A Promising Framework in Decoding of the Genome Program?," Research Article, p. 47–59.

(List continued on next page.)

Primary Examiner—W. Gary Jones
Assistant Examiner—Ethan Whisenant
Attorney, Agent, or Firm—Pennie & Edmonds LLP

[57] ABSTRACT

A method for identifying a unknown organism by comparison of the nucleotide sequence of nucleic acid in a sample with known nucleotide sequences and a determination that an unknown nucleotide sequence is present in the sample.

23 Claims, No Drawings

OTHER PUBLICATIONS

Besmer, P., Miller Jr., R.C., Caruthers, M.H., Kumar, A., Minamoto, K., Van De Sande, J.H., Sidarova, N., and Khorana, H.G., (1972), "Hybridization of Polydeoxynucleotides with Tyrosine Transfer RNA Sequences to the r–Strand of φ 80psu$_{III}$+ DNA," J. Mol. Biol., 72, 503–522.

Breslauer, K.J., Frank, R., Blocker, H., and Marky, L.A., (1986), "Predicting DNA Duplex Stability from the Base Sequence," Proc. Natl. Acad. Sci., 83, 3746–3750.

Craig, M.E., Crothers, D.M., and Doty, P., (1971), "Relaxation Kinetics of Dimer Formation by Self Complementary Oligonucleotides," J. Mol. Biol., 62, 383–401.

Craig, A.G., Nizetic, D., Hoheisel, J.D., Zehetner, G., and Lehrach, H., (1990), "Ordering of Cosmid Clones Covering the Herpes Simplex Virus Type I (HSV–I) Genome: A Test Case for Fingerprinting by Hybridisation," Nucleic Acids Research, 18(9), 2653–2660.

Drmanac, R., Lennon, G., Drmanac, S., Labat, I., Crkvenjakov, R., and Lehrach, H., (1990), "Partial Sequencing by Oligo–Hybridization: Concept and Applications in Genome Analysis," The First International Conference on Electrophoresis, Supercomputing and the Human Genome, pp. 66–70.

Gillam, S., Waterman, K., and Smith, M., (1975), "The Base–Pairing Specificity of Cellulose–pdT$_9$," Nucleic Acids Research, 2(5), 625–634.

Ikuta, S., Takagi, K., Wallace, R.B., and Itakura, K., (1987), "Dissociation Kinetics of 19 Base Paired Oligonucleotide–DNA Duplexes Containing Different Single Mismatched Base Pairs," Nucleic Acids Research, 15(2) 797–811.

Khrapko, K.R., Lysov, Y.P., Khorlyn, A.A., Shick, V.V., Florentiev, V.L., and Mirzabekov, A.D., (1989), "An Oligonucleotide Hybridization Approach to DNA Sequencing," Febs Letters, 256(1,2) 118–122.

Kohara, Y., Akiyama, K., and Isono, K., (1987), "The Physical Map of the Whole *E. coli* Chromosome: Application of a New Strategy for Rapid Analysis and Sorting of a Large Genomic Library," 50, 495–508.

Lewin, R., (1986), "Proposal to Sequence the Human Genome Stirs Debate," Research News, Molecular Biology of Homo Sapians, 232, 1598–1600.

Craig, A., Michiels, F., Zehetner, G., Sproat, B., Burmeister, M., Bucan, M., Poustka, A., Pohl, T., Frischauf, A.M., Lehrach, H., (1987), "Molecular Techniques in Mammalian Genetics: A New Era in Genetic Analysis," Human Genetics, pp. 126–132.

Wallace, R.B., Shaffer, J., Murphy, R.F., Bonner, J., Hirose, T., and Itakura, K., (1979), "Hybridization of Synthetic Oligodeoxyribonucleotides to φ $_x$174 DNA: The Effect of Single Base Pair Mismatch," Nucleic Acids Research, 6(11) 3543–3557.

Wallace, R.B., Johnson, M.J., Hirose, T., Miyake, T., Kawashima, E.H., and Itakura, K., (1981),"The Use of Synthetic Oligonucleotides as Hybridization Probes, II. Hybridization of Oligonucleotides of Mixed Sequence to Rabbit β –Globin DNA," Nucleic Acids Research, 9(4) 879–894.

Wetmur, J.G., Davidson, N., (1968), "Kinetics of Renaturation of DNA," J. Mol. Biol., 31, 349–370.

Wetmur, J.G., (1976), "Hybridization and Renaturation Kinetics of Nucleic Acids," Annual Review of Biophysics and Bioengineering, 5, 337–361.

Wood, W.I., Gitschier, J., Lasky, L.A., and Lawn, R.M., (1985), "Base Composition–Independent Hybridization in Tetramethylammonium Chloride: A Method for Oligonucleotide Screening of Highly Complex Gene Libraries," Proc. Natl. Acad. Sci. USA, 82, 1585–1588.

Angelini, G., De Preval, C., Gorski, J., and Mach, B., (1986), "High–Resolution Analysis of the Human HLA–DR Polymorphism by Hybridization with Sequence–Specific Oligonucleotide Probes," Proc. Natl. Acad. Sci. USA, 83, 4489–4493.

Berdoz, J., Gorski, Jack, Termijtelen, A.M., Dayer, J.M., Irle, C., Schendel, D., Mach, B., (1987), "Constitutive and Induced Expression of the Individual HLA–DR β and α Chain Loci in Different Cell Types," The Journal of Immunology, 139(4), 1336–1341.

Bugawan, T.L., Horn, G.T., Long, C.M., Mickelson, E., Hansen, J.A., Ferrara, G.B., Angeline, G., and Erlich, H.A., (1988), "Analysis of HLA–DP Allelic Sequence Polymorphism Using the in Vitro Enzymatic NDA Amplification of DP–α and DP–β Loci," Journal of Immunology, 141(12), 4024–4030.

Church, G.M., and Gilbert, W., (1983), "Genomic Sequencing,", Proc. Natl. Acad. Sci., 81, 1991–1995.

Crkvenjakov, R., Bucan, M., Konstantinovic, M., Fogel, M., Savic, A., and Glisin, V., (1984), "Characterization of Two Rat Globin cDNA Clones," Hemoglobin, 8(6), 597–611.

Crkenjakov, R., Drmanac, R., Bucan, M., Konstantinovic, M., Fogel, M., Maksimovic, V., Petrovic, N., Savic, A., and Glisin, V., (1984), "Cloning of Eucaryotic Gene Sequences: Studies on Human Fibroblast Interferon and Rat Globin Genes," Periodicum Biologorum, 86(2) 115–124.

Gorski, J., Tilanus, M., Giphart, M., and Mach, B., (1987), "Oligonucleotide Genotyping Shows that Alleles at the HLA–DR III Locus of the DRw52 Supertypic Group Segregate Independently of Known DR or Dw Specificities," Immunogenetics, 25, 79–83.

Irle, C., Jaques, D., Tiercy, J.M., Fuggle, S.V., Gorski, J., Termijtelen, A., Jeannet, M., and Mach, B., (1988), "Functional Polymorphism of Each of the Two HLA–DR β Chain Loci Demonstrated with Antigen–Specific DR3– and DRw52–Restricted T Cell Clones," J. Exp. Med., 167, 853–872.

Landry M.D., M.L., Fong, Ph.D., C.K.Y., (985), "Nucleic Acid Hybridization in the Diagnosis of Viral Infections," Clinics in Laboratory Medicine, 5(3), 513–529.

Lehrach, H., Zehetner, G., Nicetic, D., Craig, A., Michiels, F., (1988), "Oligonucleotide Fingerprinting, A Parallell Approach to Establish Ordered Clone Libraries," Abstracts and Papers presented at the 1988 meeting on Genome Mapping and Sequencing, p. 11.

Lehrach, H., Drmanac, R., Hoheisel, J., Larin, Z., Lennon, G., Monaco, A.P., Nizetic, D., Zehetner, G., and Poustka, A., (1990), "Hybridization Fingerprinting in Genome Mapping and Sequencing," Genome Analysis, 1, 39–71.

Michiels, F., Craig, A.G., Zehetner, G., Smith, G.P., and Lehrach, H., (1987), "Molecular Approaches to Genome Analysis: A Strategy for the Construction of Ordered Overlapping Clone Libraries," Cabios: Molecular Analysis of Genetic Distances, 3(3), 203–210.

Pevzner, P.A., (1989), "1–Tuple DNA Sequencing: Computer Analysis," Journal of Biomolecular Structure & Dynamics, 7(1), 63–73.

Rappold, G.A., Stubbs, L., Labeit, S., Crkvenjakov, R.B., and Lehrach, H., (1987), "Identification of a Testis–Specific Gene from the Mouse T–Complex Next to a CpG–rich Island," The EMBO Journal, 6(7), 1975–1980.

Saiki, R.K., Scharf, S., Faloona, F., Mullis, K.B., Horn, G.T., Erlich, H.A., Arnheim, N., (1985), "Enzymatic Amplification of $\beta$ –Globin Genomic Sequences and Restriction Site Analysis for Diagnosis of Sickle Cell Anemia," Science: Research Article, 230, 1350–1354.

Saiki, R.K., Bugawan, T.L., Horn, G.T., Mullis, K.B., and Erlich, H.A., (1986), "Analysis of Enzymatically Amplified $\beta$–Globin and HLA–DQ $\alpha$ DNA with Allele–Specific Oligonucleotide Probes," Letters to Nature, 324, 163–166.

Saiki, R.K., Walsh, P.S., Levenson, C.H., and Erlich, H.A., (1989), "Genetic Analysis of Amplified DNA with Immobilized Sequence–Specific Oligonucleotide Probes," Proc. Natl. Acad. Sci. USA, 86, 6230–6234.

Scharf, S.J., Friedmann, A., Brautbar, C., Szafer, F., Steinman, L., Horn, G., Gyllensten, U., and Erlich, H.A., (1988), "HLA Class II Allelic Variation and Susceptibility to *Pemphigus Vulgaris*," Proceedings of Natl. Academy of Science, 85, 3504–3508.

Staden, R., (1980), "A New Computer Method for the Storage and Manipulation of DNA Gel Reading Data," Nucleic Acid Research, 8, 3673–3695.

Stevanovic, M., Paunesku, T., Radosavljevic, D., Drmanac, R., and Crkvenjakov, R., (1989), "Variant Chromosomal Arrangement of Adult $\beta$ –Globin Genes in Rat," Genetics, 79, 139–150.

Sterc, J., and Novakova, V., (1988), "Role of the Limbic System in the Regulation of the Maternal Behavior in Laboratory Rats," Journal of Experimental Animal Science: XXIVth International Symposium, p. 192.

Termijtelen, A., Gorski, J., Robbins, F.M., Tanigaki, N., Tosi, R., Tilanus, M.G.J., Schroeijers, W.E.M., and Van Rood, J.J., (1988), "Correlations Between Polymorphisms at the DNA and at the Protein Level of Drw52 Haplotypes, Revealed with a Variety of Techniques," Human Immunology, 22, 171–178.

Thein, S.L., and Wallace, R.B., (1986), "The Use of Synthetic Oligonucleotides as Specific Hybridization Probes in the Diagnosis of Genetic Disorders," Human Genetic Diseases: A Practical Approach, Ch. 3, 33–50.

Tiercy, J.M., Gorski, J., Jeannet, M., and Mach, B., (1988), "Identification and Distribution of Three Serologically Undetected Alleles of HLA–DR by Oligonucleotide DNA Typing Analysis," Proc. Natl. Acad. Sci. USA, 85, 198–202.

Ucla, C., Van Rood, J.J., Gorski, J., and Mach, B., (1987), "Analysis of HLA–D Micropolymorphism by a Simple Procedure: RNA Oligonucleotide Hybridization," J. Clin. Invest., 80, 1155–1159.

Wu, D.Y., Nozari, G., Schold, M., Conner, B.J., and Wallace R.B., (1989), "Direct Analysis of Single Nucleotide Variation in Human DNA and RNA Using In Situ Dot Hybridization," Laboratory Methods: DNA, 8(2) 135–142.

Schildkraut, C.L., Marmur, J., and Doty, P., (1961), "The Formation of Hybrid DNA Moleculres and Their Use in Studies of DNA Homologies," J. Mol. Biol., 8, 595–617.

Suggs, S.V., Wallace, R.B., Hirose, T., Kawashima, E.H., and Itakura, K., (1981), "Use of Synthetic Oligonucleotides as Hybridization Probes: Isolation of Cloned cDNA Sequences for Human $\beta_2$ –Microglobulin," Proc. Natl. Acad. Sci. USA, 78(11) 6613–6617.

Evans, G.A., and Lewis, K.A., (1989), "Physical Mapping of Complex Genomes by Cosmid Multiplex Analysis," Proc. Natl. Acad. Sci. USA, 86, 5030–5034.

Sim, G.K., Kafatos, F.C., Jones, C.W., and Koehler, M.D., (1979), "Use of a cDNA Library for Studies on Evolution and Developmental Expression of the Chorion Multigene Families," Cell, pp. 1303–1316.

Stein, S.K.,(1961), "The Mathematician as an Explorer," Scientific American, 204, 149–158.

Labat, I., (1988), "Subfragments as an Informative Characteristic of the DNA Molecule–Computer Simulation," Research Report, pp. 1–33.

(1988), "Sequencing of Megabase Plus DNA by Hybridization: Theory of the Method," A poster presented at the 1988 Meeting on Genome Mapping and Sequencing, pp. III–IV.

Masiakowski et al., (1982), Cloning of cDNA Sequences of Hormone–Regulated Genes from the MCF–7 Human Breast Cancer, Nucleic Acids Research, 10(24), 7895–7903.

Lysov, et al., (1988), Determination of the DNA Nucleotide Sequence by the Hybridization with Oligonucleotides, A new method (in Russian), Doklady Akademii Nauk SSSR, 303(5), 1508–1511.

Davis et al., "Basic Methods in Molecular Biology," pp. 68–778, Elsevier Science Pub. Co. (1986).

Korn et al. DNA 3(6): pp. 421–436 (1984).

Lewin, "Genes IV," p. 489 and p. 821, OxfordUniv. Press (1990).

Lachenmeier et al., Biotechniques 13(1):pp. 124–130 (1992).

Wallace et al. Nucleic Acids Research 6: 3543–3557 (1979).

Dramanac et al. Science 260: 1649–1652 (1993).

Dramanac et al. Electrophoresis 13: 566–573 (1992).

METHOD FOR SCREENING FOR UNKNOWN ORGANISMS

CROSS-REFERENCE TO RELATED APPLICATIONS

This application is a continuation of U.S. application Ser. No. 08/332,468, filed Oct. 31 1994, now abandoned, which is a continuation of U.S. application Ser. No. 08/097,173, filed Jul. 23, 1993, now abandoned.

FIELD OF THE INVENTION

The present invention relates in general to methods for screening for a nucleic acid of an organism for which a nucleotide sequence is not known, and in particular to methods employing nucleotide sequencing for identification of organisms.

BACKGROUND

Nucleotide sequencing provides sequence information with various degrees of redundancy. The information obtained from nucleotide sequencing may be used as a source of primary sequence information about the genomes of organisms, and once the nucleotide sequence is known, may be used as a basis for obtaining expression of sequenced genes and of diagnosis of organisms containing the sequenced genes. However, there are prospective advantages for other uses for nucleotide sequencing which do not require knowledge of the existence of the organism to be sequenced.

SUMMARY OF THE INVENTION

The present invention provides a method for screening a sample containing a nucleic acid for the presence of an organism for which a nucleotide sequence is not known including: sequencing all nucleic acid in a sample; comparing the nucleotide sequence obtained in sequencing step to nucleotide sequences from known organisms; identifying a continuous run of nucleotide sequence as not corresponding to a known nucleotide sequence; and confirming the continuous run of nucleotide sequence as a nucleotide sequence of an organism for which the nucleotide sequence was not otherwise known.

A method according to the present invention may include a sequencing step including the step of sequencing the nucleic acid by hybridization with probes of known sequence.

Preferably a method according to the present invention includes a confirming step comprising the step of constructing an oligonucleotide probe having a continuous sequence of nucleotides or the complement thereto as found in the unknown sequence but not in known sequences; exposing, under stringent hybridization conditions, the labeled oligonucleotide probe to a sample suspected of containing the oligonucleotide sequence; and identifying the presence of a previously hybridization complex between the labeled oligonucleotide probe and nucleic acid in the sample. Stringent hybridization conditions are those understood in the art to result in hybridization of probes with perfectly matched, but not mismatched sequences of nucleotides.

A method according to the present invention may further comprise a second comparing step wherein a second continuous run of nucleotide sequence is compared with known nucleotide sequences.

A confirming step according to the present invention may comprise the step of: exposing the sample under stringent hybridization conditions to an oligonucleotide probe complementary to a portion of the unknown nucleotide sequence but not to a known nucleotide sequence; and separating a fraction containing a nucleic acid hybridizing to the labeled oligonucleotide from other fractions of the sample. A method according to the present invention may further include the step of microscopically examining the fraction containing the labeled oligonucleotide probe, sequencing nucleic acid in the fraction containing the labeled oligonucleotide probe, and/or a second exposing step wherein the labeled oligonucleotide probe is exposed under stringent hybridization conditions to a second sample.

A method according to the present invention may include a second exposing step comprising the step of obtaining a sample from a second individual or a second sample from the same individual.

DETAILED DESCRIPTION

Nucleic acids and methods for isolating and cloning such nucleotide sequencing are well known to those of skill in the art. See e.g., Ausubel et al., Current Protocols in Molecular Biology, Vol. 1–2, John Wiley & Sons Publs. (1989); and Sambrook et al., Molecular Cloning A Laboratory Manual, 2nd Ed., Vols. 1–3, Cold Spring Harbor Press (1989), both of which are incorporated by reference herein.

Sequencing by hybridization ("SBH") is a well developed technology that may be practiced by a number of methods known to those skilled in the art. Specifically, techniques related to sequencing by hybridization of the following documents is incorporated by reference herein: Drmanac et al., U.S. Pat. No. 5,202,231—Issued Apr. 13, 1993; Drmanac et al., Genomics, 4, 114–128 (1989); Drmanac et al., Proceedings of the First Int'l. Conf. Electrophoresis Supercomputing Human Genome Cantor, DR & Lim HA eds, World Scientific Pub. Co., Singpore, 47–59 (1991); Drmanac et al., Science, 260, 1649–1652 (1993); Lehrach et al., Genome Analysis:Genetic and Physical Mapping, 1, 39–81 (1990), Cold Spring Harbor Laboratory Press; Drmanac et al., Nucl. Acids Res., 4691 (1986); Stevanovic et al., Gene, 79, 139 (1989); Panuesku et al., Mol. Biol. Evol., 1, 607 (1990); Drmanac et al., DNA and Cell Biol., 9, 527 (1990); Nizetic et al., Nucl. Acids Res., 19, 182 (1991); Drmanac et al., J. Biomol. Struct. Dyn., 5, 1085 (1991); Hoheisel et al., Mol. Gen., 4, 125–132 (1991); Strezoska et al., Proc. Nat'l. Acad. Sci. (USA), 88, 10089 (1991); Drmanac et al., Nucl. Acids Res., 19, 5839 (1991); and Drmanac et al., Int. J. Genome Res., 1, 59–79 (1992).

SBH technology may be applied to obtain nucleotide sequence information for all or part of the genomes of known organisms. In this process, a number of oligonucleotide probes of a given length, which may be a 7-mer, are separately exposed under hybridization conditions with a sample to be sequenced. Less than the total number of possible probes of a given length may be employed using various techniques, and exposure under hybridization conditions of probes of more than one length may be employed to improve the results. SBH may be complimented by gel sequencing to obtain all of an unknown sample sequence.

According to the present invention, SBH may be applied to a sample of nucleic acid to determine whether it contains nucleic acid from at one organism for which a nucleotide sequence is unknown. Preferably, the sample may contain more than one genome. The nucleotide sequence obtained for a nucleic acid in the sample may be compared with nucleotide sequences for genomes of known organisms which may be eliminated from consideration. Continuous nucleotides sequence obtain from a sample, which sequence does not correspond to any known nucleotide sequence for a known organism, identifies the presence of a previously unknown organism.

The nucleotide sequence for the previously unknown organism that is obtained by SBH may then be used to make labeled oligonucleotide probes to diagnose the presence or absence of the organism and as an aid in identifying and isolating the previously unknown organism. Techniques such as filtration, centrifugation and chromatography may be applied to separate the organism from otherwise known organisms. Labeled oligonucleotide probes may be used as markers to identify the presence of the previously unknown organism in separatory fractions to obtain purified samples of organisms. Such purified samples of the organism may be sequenced in order to verify the original determination of the presence of a previously unknown organism and to verify the obtaining of a nucleotide sequence for the organism to whatever degree of completeness is desired.

Identification of previously unknown organisms by SBH may be employed in a diagnostic setting for determining organisms responsible for causing disease. Similarly, the method according to the present invention may be applied to identify new organisms in, for example, soil, air and water samples. Such a determination may be used to screen for organisms having a desirable or undesirable effect observed from the soil, air or water sample (such as degradation of pollutants or nitrification). Similarly, organisms having an adverse or beneficial when found effect in food may be detected by using the method of the present invention. For example, where a phenotype is desired, a microorganism which has desirable properties may be identified by SBH even out of a mixture of unknown organisms by correlating presence of hybridization with a labeled probe constructed on the basis from SBH with the presence in a sample of the desired phenotype.

EXAMPLE

A blood sample from a subject exhibiting disease symptoms screened according to the present invention. Fractions of the blood sample suspected of containing a microorganism which may be responsible for the disease symptoms are preparatively treated to obtain a cDNA library useful for screening. Such preparation may include cloning of the DNA in vectors and amplification of the cloned nucleic acid by PCR.

After application of SBH procedures, sequence information is obtained. The sequence information is in the form of stretches of nucleotide sequence representing the overlapping runs of nucleotide sequence (a run being a continuous sequence formed by overlapping more than one probe sequence) of oligonucleotide probes which hybridize to cloned DNA from the sample. Nucleotide sequences known, e.g., from GENBANK (BBN Laboratories, Inc. 10 Moulton Street, Cambridge, Mass.) or another source of nucleotide sequence information are excluded while the remaining sequences are further examined as follows.

In some instances, sequence from more than two clones may partially overlap, indicating the presence of a branch point. Such a branch point may indicate two similar stretches of nucleotide sequence in an organism in the sample, or may indicate a common portion of a sequence in two or more organisms in the sample. The sequences through each branch of the branch point are compared to known sequences. If the nucleotide sequence of a branch sequence does not correspond to a known nucleotide sequence for an organism, the determination of the nucleotide sequence of the branch is taken as an identification of an unknown organism.

Discontinuous runs of overlapping sequence which do not correspond to a nucleotide sequence from an organism for which a nucleotide sequence is known, may indicate a fragmentary sequence is present or may indicate that more than one organism is present. Such discontinuous runs of sequence are compared with nucleotide sequences from known organisms, and, to the extent that the sequence from the sample does not correspond to a known sequence, presence of at least one organism is identified.

The presence of an unknown organism is verified by synthesizing an oligonucleotide probe corresponding to a unique portion of a continuous run of nucleotide sequence identified as coming from an unknown organism or to the complement of the sequence. Such a probe is applied to the sample to confirm the presence of the determined sequence in the sample. Such a probe is applied to: another sample from the same individual from which the first sample was derived; to a sample from a second individual who has diagnostic disease symptoms similar to those of the first individual; and to a sample from a third individual who does not have diagnostic symptoms similar to those of the first individual. The presence of the nucleotide sequence but in samples from the same and the second individual but not the third individual identifies the sequence as being from a previously unknown organism.

Oligonucleotide probes are made and used to identify a fraction of a sample from an individual identified as containing the nucleic acid above. The contents of the fraction hybridizing to a labeled probe having the same or the complement of a nucleotide sequence of a previously unknown organism are examined using microscopic techniques to visually detect a previously unknown organism. Separatory techniques are applied to fractions containing the previously unknown organism to track the presence of the previously unknown organism through fractions obtain from purification procedures known to those skilled in the art, which procedures separate the previously unknown organism from known organisms in the sample.

Once separated from other organisms in the sample, sequencing by hybridization is applied to obtain a complete nucleotide sequence for the nucleic acid of the previous unknown organism.

The present invention has been described in terms of a particular embodiment. However, it is contemplated that modifications and improvements will occur to those skilled in the art upon consideration of the present specification and claims. For example, although a preferred method using SBH has been exemplified herein, gel sequencing or other nucleotide sequencing techniques may be employed solely or in combination with each other or SBH. Accordingly, it is intended that all variations and modifications of the present invention be included within the scope of the claims.

What is claimed is:

1. A method for screening for the presence of an organism for which a nucleotide sequence is not known and for confirming that said nucleotide sequence is not known, comprising the steps of:

sequencing all the nucleic acid in a sample containing nucleic acid from at least two different genomes;

comparing an entire nucleotide sequence obtained in said sequencing step to a plurality of nucleotide sequences from known organisms;

identifying the presence of the organism for which a nucleotide sequence is not known by finding a continuous run of nucleotide sequence from said sample that does not correspond to a known nucleotide sequence; and confirming the continuous run of nucleotide sequence as a nucleotide sequence of the organism for which the nucleotide sequence was not known.

2. The method as recited in claim 1, wherein said sequencing step comprises the step of sequencing the nucleic acid by hybridization with probes of known sequence.

3. The method as recited in claim 1, wherein said confirming step comprises the steps of:

constructing a labeled oligonucleotide probe having a continuous sequence of nucleotides or the complement thereto as found in the unknown nucleotide sequence but not in known nucleotide sequences;

exposing, under conditions which distinguish between an oligonucleotide probe that is exactly complementary to a target nucleic acid and an oligonucleotide probe having a single mismatched nucleotide, the labeled oligonucleotide probe to a sample suspected of containing the unknown oligonucleotide sequence; and identifying the presence of a hybridization complex between the labeled oligonucleotide probe and the previously unknown nucleic acid in the sample.

4. The method as recited in claim 1, further comprising a second comparing step wherein a second continuous run of nucleotide sequence is compared with known nucleotide sequences.

5. The method as recited in claim 1, wherein said confirming step comprises the steps of:

exposing the sample, under conditions which distinguish between an oligonucleotide probe that is exactly complementary to a target nucleic acid and an oligonucleotide probe having a single mismatched nucleotide, to a labeled oligonucleotide probe consisting of about seven nucleotides which is complementary to a portion of said unknown nucleotide sequence but not to a known nucleotide sequence; and separating a fraction containing a nucleic acid hybridizing to the labeled oligonucleotide probe from other fractions of the sample.

6. The method as recited in claim 5, further comprising the step of sequencing nucleic acid in the fraction containing the labeled oligonucleotide probe.

7. The method as recited in claim 5, further comprising a second exposing step wherein the labeled oligonucleotide probe is exposed, under conditions which distinguish between an oligonucleotide probe that is exactly complementary to a target nucleic acid and an oligonucleotide probe having a single mismatched nucleotide, to a second sample.

8. The method as recited in claim 7, wherein said second exposing step comprises the step of obtaining a sample from a second individual.

9. The method as recited in claim 7, wherein said second exposing step comprises the step of obtaining a second sample from the same individual.

10. A method for determining the presence of an unknown organism in a sample, comprising the steps of:

isolating a plurality of nucleic acids from a sample containing at least one organism;

sequencing the plurality of nucleic acids by SBH to obtain a plurality of nucleic acid sequences;

comparing the plurality of nucleic acid sequences to nucleotide sequences from known organisms; and determining the presence of at least one nucleic acid sequence that is different from all of the nucleotide sequences from known organisms, thereby determining the presence of the unknown organism in the sample.

11. A method for identifying the presence of an unknown organism in a sample, comprising the steps of:

isolating a plurality of nucleic acids from a sample containing at least two different organisms;

sequencing the plurality of nucleic acids by SBH;

comparing a plurality of sequences of the nucleic acids obtained by SBH to nucleotide sequences from known organisms;

identifying at least one unknown sequence from the sequences of the nucleic acids; and identifying the presence of an unknown organism in the sample from the unknown sequence.

12. The method of claim 11, further comprising the step of confirming the presence of an unknown organism by hybridizing an oligonucleotide probe that corresponds to a unique portion of the unknown sequence or a complement thereto with the plurality of nucleic acids from the sample containing the plurality of organisms.

13. The method of claim 10, wherein the sample with at least one organism is obtained from an individual suffering from at least one disease symptom from a microorganism infection.

14. The method of claim 13, further comprising the step of confirming the presence of an unknown organism by hybridizing an oligonucleotide probe that corresponds to a unique portion of the unknown sequence or a complement thereto with a plurality of nucleic acids from a second sample containing at least one organism.

15. The method of claim 13, further comprising the step of confirming the presence of an unknown organism by hybridizing an oligonucleotide probe that corresponds to a unique portion of the unknown sequence or a complement thereto with a plurality of nucleic acids isolated from a sample containing at least one organism obtained from a second individual suffering the at least one disease symptom from the microorganism infection.

16. The method of claim 15, further comprising the step of hybridizing the oligonucleotide probe that corresponds to a unique portion of the unknown sequence or a complement thereto with a plurality of nucleic acids isolated from a sample obtained from a third individual who does not have the at least one disease symptom from the microorganism infection.

17. The method of claim 11, further comprising the steps of:

separating the organisms in the sample into a plurality of fractions; and detecting a fraction containing the unknown organism by hybridizing the nucleic acids in the plurality of fractions with an oligonucleotide probe that corresponds to a unique portion of the unknown sequence or a complement thereto.

18. The method of claim 17, wherein said separating and detecting steps are repeated until the unknown organism is isolated from the other organisms in the sample.

19. The method of claim 18, further comprising the step of microscopically examining the isolated unknown organism.

20. The method of claim 18, further comprising the steps of:

isolating a second plurality of nucleic acids from the isolated unknown organism; and sequencing the second plurality of nucleic acids from the isolated unknown organism by SBH.

21. A method for determining the presence of an organism, comprising the steps of:
- isolating a plurality of nucleic acids randomly selected from a sample containing at least one organism;
- sequencing the plurality of nucleic acids by SBH;
- comparing a plurality of sequences from the nucleic acids obtained by SBH to a plurality of nucleotide sequences from a plurality of known organisms; and
- determining the known organism which contains the nucleotide sequences that match the sequences of the plurality of nucleic acids.

22. A method for identifying the presence of an organism in a sample containing an unknown number of organisms, comprising the steps of:
- isolating a plurality of nucleic acids from the sample;
- sequencing the plurality of nucleic acids by SBH;
- comparing a plurality of sequences of the nucleic acids obtained by SBH to nucleotide sequences from known organisms;
- identifying at least one unknown sequence from the sequences of the nucleic acids; and
- identifying the presence of an organism in the sample from the unknown sequence.

23. A method for determining the presence of an unknown organism in a sample containing at least one organism, comprising the steps of:
- isolating a plurality of nucleic acids randomly selected from the sample containing at least one organism;
- sequencing the plurality of nucleic acids by SBH;
- comparing a plurality of sequences of the nucleic acids obtained by SBH to nucleotide sequences from known organisms;
- identifying at least one unknown sequence from the sequences of the nucleic acids;
- and determining the presence of an unknown organism in the sample from the unknown sequence.

* * * * *